(12) United States Patent
Parker (10) Patent No.: US 11,554,098 B2
(45) Date of Patent: Jan. 17, 2023

(54) COMPOSITIONS COMPRISING MOLECULARLY SEPARATED CANNABINOIDS AND TERPENE BLENDS AND METHODS OF PRODUCING

(71) Applicant: HFL Partners, LLC, Westlake Village, CA (US)

(72) Inventor: Melissa Parker, Westlake Village, CA (US)

(73) Assignee: HFL Partners, LLC, Westlake Village, CA (US)

( * ) Notice: Subject to any disclaimer, the term of this patent is extended or adjusted under 35 U.S.C. 154(b) by 0 days.

(21) Appl. No.: 16/676,189

(22) Filed: Nov. 6, 2019

(65) Prior Publication Data
US 2021/0121404 A1    Apr. 29, 2021

Related U.S. Application Data

(60) Provisional application No. 62/842,901, filed on May 3, 2019.

(51) Int. Cl.
*A61K 9/14*      (2006.01)
*A61K 31/352*   (2006.01)
(Continued)

(52) U.S. Cl.
CPC .............. *A61K 9/143* (2013.01); *A61K 9/146* (2013.01); *A61K 31/015* (2013.01); *A61K 31/05* (2013.01);
(Continued)

(58) Field of Classification Search
None
See application file for complete search history.

(56) References Cited

U.S. PATENT DOCUMENTS 10,231,948 B2    3/2019  Nguyen
2018/0296616 A1*  10/2018  Rivas ................... A61K 36/185
(Continued)

FOREIGN PATENT DOCUMENTS

CA    2965493 A1   4/2016
CA    2952335      6/2017
(Continued)

OTHER PUBLICATIONS

Canadian Examiner's Report regarding Application No. 3,078,205 dated Sep. 7, 2021; 6 pages.

*Primary Examiner* — Nicole P Babson
(74) *Attorney, Agent, or Firm* — Concourse Law Group; Katherine B. Sales, Esq.

(57) ABSTRACT

An oral cannabis composition comprising molecularly separated cannabinoids, MCT oil and a terpene blend. A method of producing the oral cannabis composition comprising the steps of a) producing cannabis extract by supercritical carbon dioxide extraction; b) after step a), winterizing the cannabis extract; c) after step b), distilling the winterized cannabis extract to produce molecularly separated cannabinoids; d) after step c), mixing the molecularly separated cannabinoids with MCT oil; and e) after step d), mixing the mixture of MCT oil and molecularly separated cannabinoids with a terpene blend. A second method comprises the steps of a) selecting a desired mixture of molecularly separate cannabinoids; b) after step a), mixing the molecularly separated cannabinoids with MCT oil; and c) after step b), mixing the mixture of MCT oil and molecularly separated cannabinoids with a terpene blend.

14 Claims, 2 Drawing Sheets

(51) Int. Cl.
 *A61K 31/05* (2006.01)
 *A61K 31/122* (2006.01)
 *A61K 31/015* (2006.01)
 *A61K 9/00* (2006.01)

(52) U.S. Cl.
 CPC .......... *A61K 31/122* (2013.01); *A61K 31/352* (2013.01); *A61K 9/0053* (2013.01); *A61K 2236/37* (2013.01)

(56) References Cited

U.S. PATENT DOCUMENTS

| | | |
|---|---|---|
| 2018/0344684 A1 | 12/2018 | Vu |
| 2018/0369192 A1 | 12/2018 | Green |
| 2019/0015383 A1 | 1/2019 | Woelfel |
| 2019/0022229 A1* | 1/2019 | Manalo .................. A61K 31/05 |
| 2019/0133993 A1 | 5/2019 | Cranford |
| 2019/0134122 A1* | 5/2019 | Pertile .................. A61K 31/047 |

FOREIGN PATENT DOCUMENTS

| | | |
|---|---|---|
| CA | 3024645 | 1/2019 |
| CA | 3076963 A1 | 6/2019 |
| CA | 3033404 A1 | 8/2020 |
| WO | 2018023163 | 2/2018 |
| WO | 201903623 | 2/2019 |

\* cited by examiner

COMPOSITIONS COMPRISING MOLECULARLY SEPARATED CANNABINOIDS AND TERPENE BLENDS AND METHODS OF PRODUCING

CROSS-REFERENCE TO RELATED APPLICATION

This patent application claims the benefit of United States Provisional Patent Application Ser. No. 62/842,901 entitled "Hemp Distillate with Terpene Blends" filed May 3, 2019, which application is incorporated in its entirety herein by this reference.

BACKGROUND OF THE INVENTION

Many users have the desire for cannabis compositions with consistent and targeted effects. However, this is difficult to achieve because there are over 800 known cultivars, each comprising unique plant molecule assortments. Even within the same cultivar, the chemical composition will vary each time it is grown due to environmental factors and mutation. The chemical composition of the plant has a profound effect on the user's experience as it relates to flavor and scent, as well as induced therapeutic benefit (examples: mood, energy level, mental acuity, pain relief, etc.). Due to the plant's inconsistent chemical composition, it is difficult to achieve cannabis compositions that have consistent effects from batch to batch.

As such, there is a need for improved cannabis compositions that produce targeted and consistent effects.

The present invention overcomes several of the deficiencies, disadvantages and undesired parameters associated with known cannabis compositions and methods of producing same.

SUMMARY OF THE INVENTION

According to one embodiment of the present invention, there is provided an oral cannabis composition comprising molecularly separated cannabinoids distillate; MCT oil; and a terpene blend.

Optionally, the oral cannabis composition comprises 500 mg of molecularly separated cannabinoids; 14 ml of MCT oil; and a terpene blend comprising:
Alpha-pinene at about 15.75 mg/g;
Beta-caryophyllene at about 100.63 mg/g;
Beta-pinene at about 15.75 mg/g;
Humulene at about 26.25 mg/g;
Myrcene at about 158.38 mg/g;
Limonene at about 26.25 mg/g;
Linalool at about 52.50 mg/g;
Terpinolene at about 21.00 mg/g; and
Other terpenoids at about 458.49 mg/g.
Optionally, the terpene blend comprises:
Alpha-pinene at about 269.37 mg/g;
Beta-caryophyllene at about 109.66 mg/g;
Beta-pinene at about 106.93 mg/g;
Alpha-humulene at about 26.07 mg/g;
Myrcene at about 352.62 mg/g;
Alpha-bisabolol at about 18.21 mg/g;
Borneol at about 1.81 mg/g;
Valencene at about 0.87 mg/g;
Nerolidol at about 1.98 mg/g;
Linalool at about 7.61 mg/g;
Limonene at about 38.35 mg/g;
Fenchol at about 4.04 mg/g;
Alpha-phellandrene at about 16.76 mg/g;
Caryophyllene Oxide at about 0.98 mg/g;
Terpineol at about 3.68 mg/g;
R-(+)-pulegone at about 0.23 mg/g;
Citronellol at about 0.96 mg/g; and
Phytol at about 17.08 mg/g.
Optionally, the terpene blend comprises:
Alpha-pinene at about 22.95 mg/g;
Beta-caryophyllene at about 147.53 mg/g;
Beta-pinene at about 2.97 mg/g;
Alpha-humulene at about 228.05 mg/g;
Myrcene at about 143.64 mg/g;
Valencene at about 0.52 mg/g;
Linalool at about 396.42 mg/g;
Terpinolene at about 2.98 mg/g;
Nerolidol at about 9.95 mg/g;
Fenchol at about 0.97 mg/g;
Alpha-phellandrene at about 7.86 mg/g; and
Caryophyllene Oxide at about 12.35 mg/g.
Optionally, the terpene blend comprises:
Alpha-pinene at about 246.02 mg/g;
Beta-caryophyllene at about 4.66 mg/g;
Beta-pinene at about 77.84 mg/g;
Alpha-Humulene at about 6.05 mg/g;
Myrcene at about 419.53 mg/g;
Limonene at about 35.48 mg/g;
Valencene at about 6.36 mg/g;
Camphene at about 6.72 mg/g;
Eucalyptol at about 22.08 mg/g;
Alpha-phellandrene at about 23.59 mg/g;
Caryophyllene Oxide at about 70.62 mg/g; and
Phytol at about 0.25 mg/g.
Optionally, the terpene blend comprises:
Alpha-pinene at about 84.10 mg/g;
Beta-caryophyllene at about 133.80 mg/g;
Beta-pinene at about 52.90 mg/g;
Humulene at about 54.50 mg/g;
Myrcene at about 36.70 mg/g;
Limonene at about 180.70 mg/g;
Linalool at about 30.20 mg/g;
Terpinolene at about 17.30 mg/g; and
Other terpenoids at about 392.00 mg/g.

According to another embodiment, there is provided an oral cannabis composition produced by a method comprising the steps of:
a) producing cannabis extract by supercritical carbon dioxide extraction;
b) after step a), winterizing the cannabis extract;
c) after step b), distilling the winterized cannabis extract to produce the molecularly separated cannabinoids;
d) after step c), mixing the molecularly separated cannabinoids to the desired ratios with heated MCT oil;
e) after step d), cooling the mixture of MCT oil and molecularly separated cannabinoids; and
f) after step e), mixing the mixture of MCT oil and molecularly separated cannabinoids with a terpene blend.

According to another embodiment, there is provided an oral cannabis composition produced by a method comprising the steps of:
A) selecting a desired mixture of molecularly separated cannabinoids;
B) after step a), mixing the molecularly separated cannabinoids with MCT oil heated to approximately 110 degrees Fahrenheit;
C) after step b), cooling the mixture of the MCT oil and molecularly separated cannabinoids; and D) after step c), mixing the mixture of MCT oil and molecularly separated cannabinoids with a terpene blend.

DRAWINGS

These and other features, aspects and advantages of the present invention will become better understood with reference to the following description, appended claims, and accompanying drawings where:

DETAILED DESCRIPTION OF THE INVENTION

The following discussion describes in detail one embodiment of the present invention and several variations of that embodiment. This discussion should not be construed, however, as limiting the invention to those particular embodiments. Practitioners skilled in the art will recognize numerous other embodiments as well.

Definitions

As used herein, the following terms and variations thereof have the meanings given below, unless a different meaning is clearly intended by the contest in which such term is used.

The terms "a," "an," and "the" and similar referents used herein are to be construed to cover both the singular and the plural unless their usage in context indicates otherwise.

As used in this disclosure, the term "comprise" and variations of the term, such as "comprising" and "comprises," are not intended to exclude other additives, components, integers ingredients or steps.

The term "cannabinoids" refers to any of a group of closely related compounds which include cannabinol and the active constituents of cannabis.

The term "terpenes" refers to any of a large group of volatile unsaturated hydrocarbons found in the essential oils of plants, especially conifers and citrus trees. They are based on a cyclic molecule having the formula $C_{10}H_{16}$.

The Invention

The invention as discussed in this application is with respect to compositions comprising molecularly separated cannabinoids and terpene blends and methods of producing same. Molecularly separated means the cannabinoids have been molecularly separated from the rest of the cannabis compounds. Alternatively, molecularly separated can also mean that the cannabinoids were isolated from other cannabinoids.

There are multiple embodiments of compositions and methods presented in this application.

Figure 1:
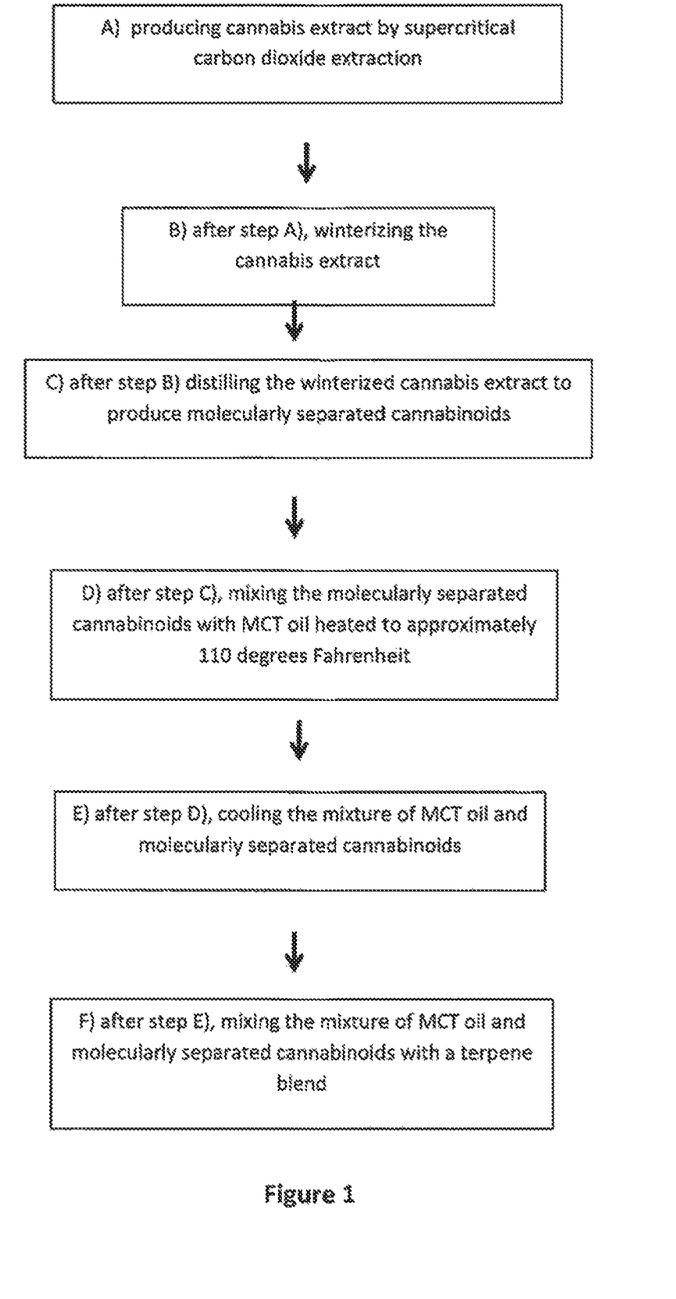
FIG. 1 is a flow chart of a method of producing a composition having features of the present invention.

Referring now to FIG. 1, there is shown a first method of producing an oral cannabis composition of the present invention. The steps are as follows:

First, cannabis extract is produced by supercritical carbon dioxide ($CO_2$) extraction.

Second, the cannabis extract is winterized.

Third, the winterized cannabis extract is distilled. Steps 1-3 remove all of the naturally occurring terpenes from the extract and produce molecularly separated cannabinoids. At this stage, the desired molecularly separate cannabinoids are then selected. The molecularly separate cannabinoids selected can either comprise the naturally occurring cannabinoid amounts/ratios that were collected from that specific plant extract, or a specific formula/ratio of molecularly separated cannabinoids, collected at a different time, possibly during a different process, and designed to achieve a desired effect for the end user can be selected for use.

Fourth, a specific blend of terpenes is added to the molecularly separated cannabinoids to produce the cannabis composition of the present invention.

The supercritical $CO_2$ extraction process creates phase changes in carbon dioxide utilizing temperature and pressure. $CO_2$ is known as a "tunable solvent" making it extremely versatile for creating a multitude of end products by controlling temperature and pressure. These phase changes create an environment to drop out differing weights of components in the plant material. One of the most amazing things about extracting with $CO_2$ is the ability to separate individual compounds as the extraction is taking place. Fractionation is accomplished in this system by having a series of extract separators in line. Fractionation is a separation process in which a certain quantity of a mixture (gas, solid, liquid, enzymes, suspension, or isotope) is divided during a phase transition, into a number of smaller quantities (fractions) in which the composition varies according to a gradient. As the extract laden $CO_2$ exits the extractor vessel it cascades through these separators. The first separator is set at the highest pressure in the series. The 2nd and 3rd separators ramp downwards in pressure. Different molecular weight compounds drop out at different temperatures and pressures thus allowing for the fractionation to take place in individual separators.

Carbon dioxide is a supercritical fluid, meaning it converts to a liquid when placed under extreme pressure. As such, it is able to remove essential oils from plant matter (in this case cannabis) without leaving residues behind.

Winterization is the process of mixing the raw cannabis extract with warm (approximately 50 degrees Celsius) ethanol to filter out the undesired plant waxes and lipids. The raw extract is mixed with approximately 10 ml ethanol per 1 g of raw extract and then frozen. Once frozen, waxes and lipids separate from the raw extract. At that point the mixture is put through a vacuum filtration system that removes the plant waxes and lipids leaving behind refined extract. This process creates a superior oil extract, reaching a rate of up to 65% cannabinoid potency.

Short path distillation separates and refines valuable molecules (cannabinoids and terpenes), from unwanted plant matter as well as contaminants, resulting in a clean and practically transparent concentrate. In comparison with other refinement means, the distillate is in a level above because it obtains a pure oil of very high cannabinoid potency (usually 75% or more). The distillation process involves gradually heating the winterized extract in a feed flask with a heating mantle. The desired plant molecules (cannabinoids and terpenes) get vaporized and rise up through the distillation head, leaving the plant waste and remaining solvents behind. A vacuum is applied to assist in drawing the vapors up into the fractionating tubing. From the fractionating tubing the contents then hit the condensing tube where the fractions take separate paths determined by the weight of each fraction. One collection flask will collect the terpenes and the other will collect the cannabinoids.

This process is repeated a plurality of times to create pure cannabinoids without chlorophyll, lipids, waxes, other undesired plant matter, or residual solvents. Preferably, the distillation process is completed at least three times and up to as many times necessary to achieve the desired purity. Also in this process, the cannabinoids are decarboxylated. All cannabinoids contained within the trichomes of raw cannabis flowers have an extra carboxyl ring or group (COOH) attached to their chain. For example, tetrahydrocannabinolic acid (THCA) is synthesized in prevalence within the trichrome heads of freshly harvested cannabis flowers. In most regulated markets, cannabis distributed in dispensaries contains labels detailing the product's cannabinoid contents. THCA, in many cases, prevails as the highest cannabinoid present in items that have not been decarboxylated (e.g., cannabis flowers and concentrates).

THCA has a number of known benefits when consumed, including having anti-inflammatory and neuroprotective qualities. But THCA is not intoxicating, and must be converted into THC through decarboxylation before any effects can be felt. An example of decarboxylation is all of the CBDa molecules are converted into CBD.

Steps a)-c) remove all of the naturally occurring terpenes from the extract and produce molecularly separated cannabinoids. As noted above, step c) produces molecularly separate cannabinoids. At this stage, the desired molecularly separate cannabinoids are then selected. The molecularly separate cannabinoids selected can either comprise the naturally occurring cannabinoid amounts/ratios that were collected from that specific plant extract, or a specific formula/ratio of molecularly separated, collected at a different time, possibly during a different process, and designed to achieve a desired effect for the end user can be selected for use.

Alternatively, the method of producing an oral cannabis composition of the present invention can start with the step of selecting a mixture/formula/ratio of molecularly separated cannabinoids, rather than the actual production of the molecularly separated cannabinoids.

Once the molecularly separated cannabinoids have been produced (and/or the desired mixture selected), they are mixed with medium-chain triglyceride (MCT) oil (preferably derived from coconut, but optionally olive oil, avocado oil, almond oil or palm oil could be used, just to name a few). Due to their shorter length, medium-chain triglycerides are easily digested and there are many health benefits that are linked to the way the human body processes these fats. Preferably the MCT oil is heated to approximately 110 degrees Fahrenheit. The mixture of molecularly separated cannabinoids and MCT oil is then cooled and mixed with the desired terpene blend to produce the desired effect.

Figure 2:
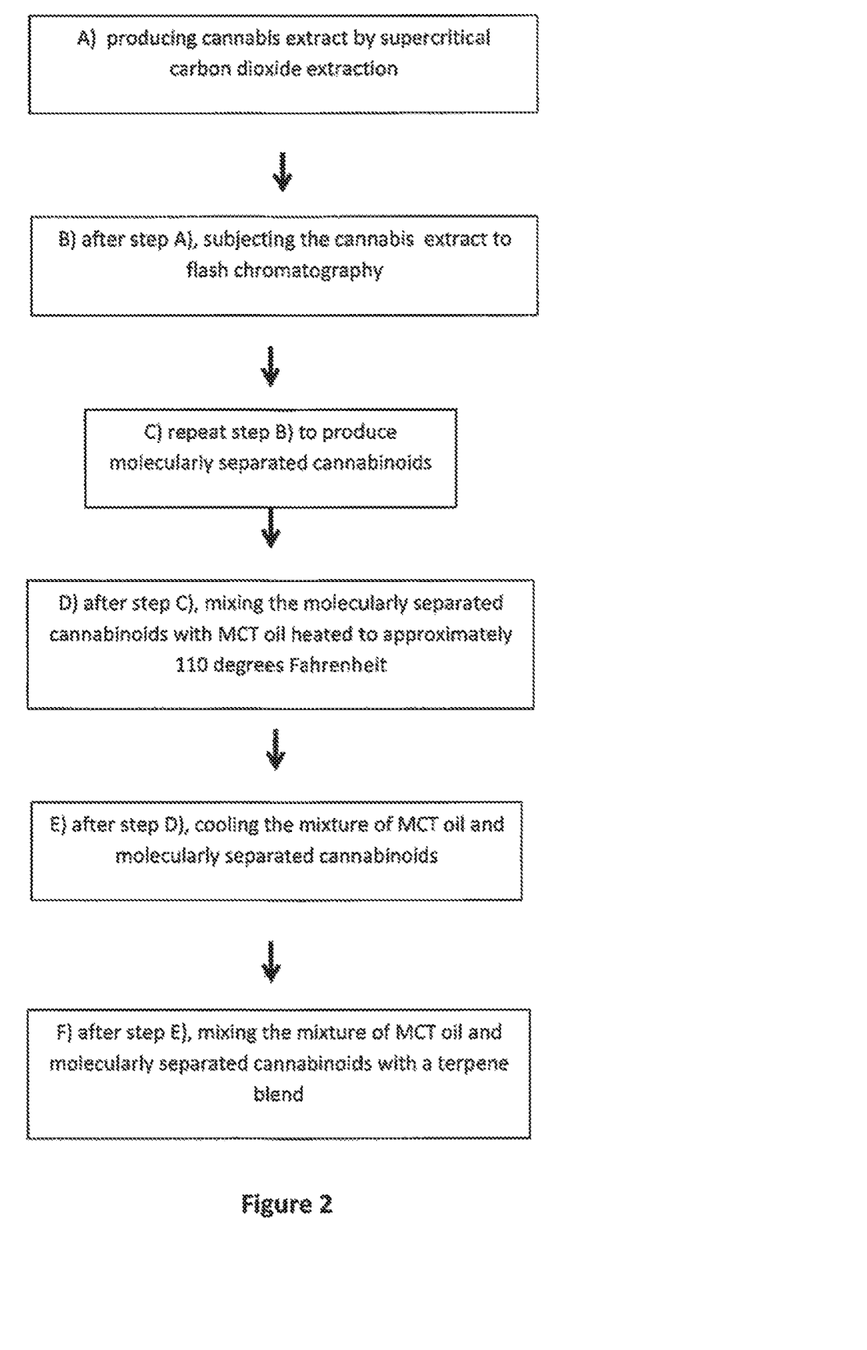
FIG. 2 is a second flow chart of a second method of producing a composition having features of the present invention.

Referring now to FIG. 2, there is shown a second method of producing the composition of the present invention. The second method comprises the steps of: First, extracting cannabis extract by supercritical CO2 extraction (same as discussed above), and second, subjecting the cannabis extract to flash chromatography, wherein the process of flash chromatography is repeated at least twice.

Flash chromatography is a type of rapid preparative column chromatography where 0.1-10 g of mixture is separated in less than 15 minutes by using pressurized gas to drive the mobile phase through the column. In flash chromatography, gravity or some external source of pressure pushes the mobile phase through the column which is packed with a solid stationary phase. The cannabis compounds interact with the solid stationary phase for differing amounts of time, and are eluted in order of increasing polarity in the column.

Flash chromatography is a method to easily separate complex mixtures of compounds. It is based on column chromatography, which is a technique to purify (separate) compounds based on polarity and hydrophobicity. Separation occurs between differential partitioning between a mobile phase and a stationary phase. If a liquid such as cannabis extract is subjected to this separation technique, the results will be separated solvents, cannabinoids, terpenes, and other plant waste. Preferably, the flash chromatography process is repeated at least twice to produce molecularly separated cannabinoids. At this point, the desired cannabinoids are collected and the unwanted molecules are discarded. As noted above, the maker of the composition then selects what molecularly separated cannabinoids they would like to use. Either the naturally occurring cannabinoids that were collected, or a specific cannabinoid formula designed to achieve a specific effect for the end user.

As noted above, once the molecularly separated cannabinoids have been produced, they are mixed with MCT oil. Preferably the MCT oil is heated to approximately 110 degrees Fahrenheit. The mixture of molecularly separated cannabinoids and MCT oil is then cooled and mixed with the desired terpene blend to produce the desired effect.

Other ways to create a cannabis extract include: solution extraction, pressurized liquid extraction, and microwave extraction, to name a few.

Botanical terpenes can be extracted via steam, expression, vacuum distillation or through chromatography. They are then fractionally purified and the molecules am isolated. Once the terpenes are isolated they are mixed into the desired unique terpene blend formulas.

The final blended formulas are to be taken orally via one of the following methods:

By spray, by dropper, by edible cannabis product, by capsule or by other oral means. If the composition is delivered by spray, usually one spray (0.2 ml) is equivalent to one dose and will have approximately 6.67 mg molecularly separated cannabinoids distillate and 2.25 mg of blended terpenes. Consumer is to shake the bottle well before using. Then spray one time in mouth. They are to start with a low dose and work their way up as needed. Daily use is recommended for best results.

EXAMPLES

In a first embodiment, the invention comprises an oral cannabis composition that is intended to aid the user with occasional and non-disease related sleep issues. The first composition comprises approx. 500 mg of molecularly separated cannabinoids distillate, approximately 14 ml of MCT oil, and a terpene blend (1-2% of total volume) comprising a total concentration of terpenoids of approximately 875 mg/g.

The preferred terpene blend for the first composition is as follows:

| Ingredient | Amount |
| --- | --- |
| Alpha-pinene | 15.75 mg/g |
| Beta-caryophyllene | 100.63 mg/g |
| Beta-pinene | 15.75 mg/g |
| Humulene | 26.25 mg/g |
| Limonene | 26.25 mg/g |
| Linalool | 52.50 mg/g |
| Myrcene | 158.38 mg/g |
| Terpinolene | 21.00 mg/g |
| Other terpenoids | 458.49 g mg/g |

However, the first composition is not limited to the preferred terpene blend noted above. The terpene blend for the first composition can comprise the following ranges of components, wherein the components can comprise any number within the following ranges-alpha-pinene from about 0 mg/g to about 40.73 mg/g, beta-caryophyllene from about 75.63 mg/g to about 125.63 mg/g, beta-pinene from about 0 mg/g to about 40.75 m/g, humulene from about 1.25 mg/g to about 51.25 mg/g, limonene from about 1.253 mg/g to about 51.25 mg/g, linalool from about 27.30 mg/g to about 77.50 mg/g, myrcene from about 133 mg/g to about 183.39 mg/g, terpinolene from about 0 mg/g to about 46.00 mg/g, and other terpenoids from about 45.4 mg/g to about 458.5 mg/g.

In a second embodiment, the invention comprises an oral cannabis composition that is intended to aid the user with occasional and non-disease related stress. The second composition comprises 500 mg of molecularly separated cannabinoids distillate, approximately 14 ml of MCT oil, and a terpene blend (1-2% of total volume) comprising a total concentration of terpenoids of approximately 977.37 mg/g.

The preferred terpene blend for the second composition is as follows:

| Ingredient | Amount |
| --- | --- |
| Alpha-bisabolol | 18.21 mg/g |
| Alpha-pinene | 269.37 mg/g |
| Borneol | 1.81 mg/g |
| Beta-caryophyllene | 109.66 mg/g |
| Alpha-humulene | 26.07 mg/g |
| Valencene | 0.87 mg/g |
| Nerolidol | 1.98 mg/g |
| Linalool | 7.61 mg/g |
| Limonene | 38.35 mg/g |
| Myrcene | 352.62 mg/g |
| Fenchol | 4.04 mg/g |
| Alpha-phellandrene | 16.76 mg/g |
| Caryophyllene Oxide | 0.98 mg/g |
| Terpineol | 3.68 mg/g |
| Beta-pinene | 106.93 mg/g |
| R-(+)-pulegone | 0.23 mg/g |
| Citronellol | 0.96 mg/g |
| Phytol | 17.08 mg/g |

However, the second composition is not limited to the preferred terpene blend noted above. The terpene blend for the second composition can comprise the following ranges of components, wherein the components can comprise any number within the following ranges: alpha-bisabolol from about 0 mg/g to about 43.21 mg/g, alpha-pinene from about 244.37 mg/g to about 294.37 mg/g, borneol from about 0 mg/g to about 26.81 mg/g, beta-caryophyllene from about 84.66 mg/g to about 134.66 mg/g, alpha-humulene from about 1.07 mg/g to about 51.07 mg/g, valencene from about 0 mg/g to about 25.87 mg/g, nerolidol from about 0 mg/g to about 26.98 mg/g, linalool from about 0 mg/g to about 32.61 mg/g, limonene from about 13.35 mg/g to about 63.35 mg/g, myrcene from about 327.62 mg/g to about 377.62 mg/g, fenchol from about 0 mg/g to about 29.04 mg/g, alpha-phellandrene from about 0 mg/g to about 41.76 mg/g, caryophyllene Oxide from about 0 mg/g to about 25.98 mg/g, terpineol from about 0 mg/g to about 28.68 mg/g, beta-pinene from about 81.93 mg/g to about 131.93 mg/g, R-(+)-pulegone from about 0 mg/g to about 25.23 mg/g, citronellol from about 0 mg/g to about 25.96 mg/g and phytol from about 17.05 mg/g to about 17.1 mg/g.

In a third embodiment, the invention comprises an oral cannabis composition that is intended to aid the user with the detox of toxins. The third composition comprises 500 mg of molecularly separated cannabinoids distillate, approximately 14 ml of MCT oil, and a terpene blend (1-2% of total volume) comprising a total concentration of terpenoids of approximately 976.20 mg/g.

The terpene blend for the third composition is as follows:

| Ingredient | Amount |
| --- | --- |
| Alpha-pinene | 22.95 mg/g |
| Beta-caryophyllene | 147.53 mg/g |
| Beta-pinene | 2.97 mg/g |
| Alpha-humulene | 228.05 mg/g |
| Valencene | 0.52 mg/g |
| Linalool | 396.42 mg/g |
| Myrcene | 143.64 mg/g |
| Terpinolene | 2.98 mg/g |
| Nerolidol | 9.95 mg/g |
| Fenchol | 0.97 mg/g |
| Alpha-phellandrene | 7.86 mg/g |
| Caryophyllene Oxide | 12.35 mg/g |

However, the third composition is not limited to the preferred terpene blend noted above. The terpene blend for the third composition can comprise the following ranges of components, wherein the components can comprise any number within the following ranges: alpha-pinene from about 0 mg/g to about 47.95 mg/g, beta-caryophyllene from about 122.53 mg/g to about 172.53 mg/g, beta-pinene from about 0 mg/g to about 27.97 mg/g, alpha-humulene from about 203.05 mg/g to about 253.05 mg/g, valencene from about 0 mg/g to about 25.52 mg/g, linalool from about 371.42 mg/g to about 421.42 mg/g, myrcene from about 118.64 to about 168.64 mg/g, terpinolene from about 0 mg/g to about 27.98 mg/g, nerolidol from about 0 mg/g to about 34.95 mg/g, fenchol from about 0 mg/g to about 25.97 mg/g, alpha-phellandrene from about 0 mg/g to about 32.6 mg/g, and caryophyllene oxide from about 12.32 mg/g to about 12.37 mg/g.

In a fourth embodiment, the invention comprises an oral cannabis composition that is intended to aid the user with occasional and non-disease related pain. The fourth composition comprises 500 mg of molecularly separated cannabinoids distillate, approximately 14 ml of MCT oil, and a terpene blend (1-2% of total volume) comprising a total concentration of terpenoids of approximately 919.20 mg/g.

The terpene blend for the fourth composition is as follows:

| Ingredient | Amount |
| --- | --- |
| Alpha-pinene | 246.02 mg/g |
| Beta-caryophyllene | 4.66 mg/g |
| Beta-pinene | 77.84 mg/g |
| Alpha-Humulene | 6.05 mg/g |
| Limonene | 35.48 mg/g |
| Valencene | 6.36 mg/g |
| Myrcene | 419.53 mg/g |
| Camphene | 6.72 mg/g |
| Eucalyptol | 22.08 mg/g |
| Alpha-phellandrene | 23.59 mg/g |
| Caryophyllene Oxide | 70.62 mg/g |
| Phytol | 0.25 mg/g |

However, the fourth composition is not limited to the preferred terpene blend noted above. The terpene blend for the fourth composition can comprise the following ranges of components, wherein the components can comprise any number within the following ranges: alpha-pinene from about 221.02 mg/g to about 271.02 mg/g, beta-caryophyllene from about 0 mg/g to about 29.66 mg/g, beta-pinene from about 52.84 mg/g to about 102.84 mg/g, alpha-humulene from about 0 mg/g to about 31.05 mg/g, limonene from about 10.48 mg/g to about 60.49, valencene from about 0 mg/g to about 31.36 mg/g, myrcene from about 394.53 mg/g to about 444.53 mg/g, camphene from about 0 mg/g to about 31.72 mg/g, eucalyptol from about 0 mg/g to about 47.08 mg/g, alpha-phellandrene from about 0 mg/g to about 48.59 mg/g, caryophyllene oxide from about 45.62 mg/g to about 95.62 mg/g, and phytol from about 0 mg/g to about 25.25 mg/g.

In a fifth embodiment, the invention comprises an oral cannabis composition that is intended to aid the user with occasional and non-disease related focusing issues. The fifth composition comprises 500 mg of molecularly separated cannabinoids distillate, approximately 14 ml of MCT oil, and a terpene blend (1-2% of total volume) comprising a total concentration of terpenoids of approximately 982.20 mg/g.

The terpene blend for the fifth composition is as follows:

| Ingredient | Amount |
| --- | --- |
| Alpha-pinene | 84.10 mg/g |
| Beta-caryophyllene | 133.80 mg/g |
| Beta-pinene | 52.90 mg/g |
| Humulene | 54.50 mg/g |
| Limonene | 180.70 mg/g |
| Linalool | 30.20 mg/g |
| Myrcene | 36.70 mg/g |
| Terpinolene | 17.30 mg/g |
| Other terpenoids | 392.0 mg/g |

However, the fifth composition is not limited to the preferred terpene blend noted above. The terpene blend for the fifth composition can comprise the following ranges of components, wherein the components can comprise any number within the following ranges: alpha-pinene from about 59.10 mg/g to about 109.10 mg/g, beta-caryophyllene from about 108.90 mg/g to about 158.80 mg/g, beta-pinene from about 27.90 mg/g to about 77.90 mg/g, humulene from about 29.50 mg/g to about 79.50 mg/g, limonene from about 155.70 mg/g to about 205.70 mg/g linalool from about 5.20 mg/g to about 55.20 mg/g, myrcene from about 11.70 mg/g to about 61.70 mg/g, terpinolene from about 0 mg/g to about 32.30 mg/g, and other terpenoids from about 367.00 mg/g to about 417.00 mg/g.

An additional embodiment of the present invention is a powder comprising the combination of the molecularly separated cannabinoids and terpene blends (without the MCT oil) for use in a topical product, food, beverage, capsule, pressed tablet, or orally dissolvable tablet. The process of converting the liquid molecularly separated cannabinoids and terpene blend mixture to powder is designed to ensure the integrity of the molecules during the conversion process while converting it into a fie-flowing powder.

There are several ways to achieve the fee-flowing powder; however, the preferred method uses gravity to introduce both the liquid (mixture of molecularly separate cannabinoids and terpene blend) and desired carrier into a nitrogen-rich and controlled environment, at room temperature to force the liquid into the carrier medium. There is no heat or oxygen contamination during the conversion process, which reduces the risk of oxidation, maintains low peroxide values, and creates a stable powder. The desired carrier can be selected from, although not limited to, the following: maltodextrin, tapioca maltodextrin, cellulose, silica, calcium carbonate, whey protein, and others.

In this embodiment, the same ingredients from the liquid version of the invention are used (molecularly separated cannabinoids and terpene blends) to create a solid form; without changing the molecules or formula. This "solid" form of the invention may be preferred over the liquid form by some consumers. The "solid" form offers ease of use, portability, and may be preferable for those users with physical limitations. As noted above, making the formulation of the present invention into a solid form allows for other applications such as dissolvable tablets, pressed tablets, encapsulation, food and drink additives, and topical applications.

Advantages of the Present Invention

Providing a targeted and consistent cannabis composition product. Currently, cannabis products on the market vary from batch to batch in their cannabinoid and terpene content. This is because the naturally occurring terpene blend found in cannabis plants can vary widely from plant to plant and from cultivation center to cultivation center. By removing all of the naturally occurring terpenes and only adding back in a very specific formula of terpenes, the present invention provides a consistent and reliable cannabis composition that can provide very specific effects, usually for therapeutic purposes. As noted above, the five different terpene blends disclosed above provide five different very specific effects for the user. This ensures that each batch has the same controlled and consistent outcome. Effects can also be controlled by using a specific cannabinoid formula.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure. All references cited herein are incorporated by reference in their entirety.

What is claimed is:
1. A method of producing an oral cannabis composition, the method consisting of the steps of:
   a) producing cannabis extract;
   b) after step a) winterizing the cannabis extract;
   c) after step b) distilling the winterized cannabis extract to remove all naturally occurring terpenes from the cannabis extract, thereby producing molecularly separated cannabinoids;
   d) mixing the molecularly separated cannabinoids with a heated MCT oil;
   e) after step d), cooling the mixture of the heated MCT oil and molecularly separated cannabinoids; and
   f) after step e), mixing the mixture of MCT oil and molecularly separated cannabinoids with a terpene blend, wherein the terpene blend is selected to produce a target effect on the user, wherein the terpene blend consists of:
      a) Alpha-pinene at about 15.75 mg/g;
      b) Beta-caryophyllene at about 100.63 mg/g;
      c) Beta-pinene at about 15.75 mg/g;
      d) Humulene at about 26.25 mg/g;
      e) Myrcene at about 158.38 mg/g;
      f) Limonene at about 26.25 mg/g;
      g) Linalool at about 52.50 mg/g;
      h) Terpinolene at about 21.00 mg/g; and
      i) Other terpenoids at about 458.49 mg/g.

2. The method of claim 1, further comprising the step of:
g) forcing the mixture of MCT oil, molecularly separated cannabinoids, and terpene blend into a carrier medium to create a powder.

3. The method of claim 2, wherein the carrier medium is one or more of maltodextrin, cellulose, silica, calcium carbonate, and whey protein.

4. The method of claim 1, wherein the oral cannabis composition produced by the method consists of:
 a) 500 mg of molecularly separated cannabinoids;
 b) 14 ml of MCT oil; and
 c) a terpene blend consisting of:
  1) Alpha-pinene at about 15.75 mg/g;
  2) Beta-caryophyllene at about 100.63 mg/g;
  3) Beta-pinene at about 15.75 mg/g;
  4) Humulene at about 26.25 mg/g;
  5) Myrcene at about 158.38 mg/g;
  6) Limonene at about 26.25 mg/g;
  7) Linalool at about 52.50 mg/g;
  8) Terpinolene at about 21.00 mg/g; and
  9) Other terpenoids at about 458.49 mg/g.

5. The method of claim 1, wherein the molecularly separated cannabinoids of step d) comprise naturally occurring cannabinoid amounts and/or ratios that were produced from step c), and are designed to achieve a desired effect for the end user.

6. A method of producing an oral cannabis composition, the method consisting of the steps of:
 a) producing cannabis extract;
 b) after step a) winterizing the cannabis extract;
 c) after step b) distilling the winterized cannabis extract to remove all naturally occurring terpenes from the cannabis extract, thereby producing molecularly separated cannabinoids;
 d) mixing the molecularly separated cannabinoids with a heated MCT oil;
 e) after step d), cooling the mixture of the heated MCT oil and molecularly separated cannabinoids; and
 f) after step e), mixing the mixture of MCT oil and molecularly separated cannabinoids with a terpene blend, wherein the terpene blend is selected to produce a target effect on the user, wherein the terpene blend of step f) consists of:
  a) Alpha-pinene at about 22.95 mg/g;
  b) Beta-caryophyllene at about 147.53 mg/g;
  c) Beta-pinene at about 2.97 mg/g;
  d) Alpha-humulene at about 228.05 mg/g;
  e) Myrcene at about 143.64 mg/g;
  f) Valencene at about 0.52 mg/g;
  g) Linalool at about 396.42 mg/g;
  h) Terpinolene at about 2.98 mg/g;
  i) Nerolidol at about 9.95 mg/g;
  j) Fenchol at about 0.97 mg/g;
  k) Alpha-phellandrene at about 7.86 mg/g; and
  l) Caryophyllene Oxide at about 12.35 mg/g.

7. A method of producing an oral cannabis composition, the method consisting of the steps of:
 a) producing cannabis extract;
 b) after step a) winterizing the cannabis extract;
 c) after step b) distilling the winterized cannabis extract to remove all naturally occurring terpenes from the cannabis extract, thereby producing molecularly separated cannabinoids;
 d) mixing the molecularly separated cannabinoids with a heated MCT oil;
 e) after step d), cooling the mixture of the heated MCT oil and molecularly separated cannabinoids; and
 f) after step e), mixing the mixture of MCT oil and molecularly separated cannabinoids with a terpene blend, wherein the terpene blend is selected to produce a target effect on the user, wherein the terpene blend of step f) consists of:
  a) Alpha-pinene at about 246.02 mg/g;
  b) Beta-caryophyllene at about 4.66 mg/g;
  c) Beta-pinene at about 77.84 mg/g;
  d) Alpha-Humulene at about 6.05 mg/g;
  e) Myrcene at about 419.53 mg/g;
  f) Limonene at about 35.48 mg/g;
  g) Valencene at about 6.36 mg/g;
  h) Camphene at about 6.72 mg/g;
  i) Eucalyptol at about 22.08 mg/g;
  j) Alpha-phellandrene at about 23.59 mg/g;
  k) Caryophyllene Oxide at about 70.62 mg/g; and
  l) Phytol at about 0.25 mg/g.

8. A method of producing an oral cannabis composition, the method consisting of the steps of:
 a) producing cannabis extract;
 b) after step a) winterizing the cannabis extract;
 c) after step b) distilling the winterized cannabis extract to remove all naturally occurring terpenes from the cannabis extract, thereby producing molecularly separated cannabinoids;
 d) mixing the molecularly separated cannabinoids with a heated MCT oil;
 e) after step d), cooling the mixture of the heated MCT oil and molecularly separated cannabinoids; and
 f) after step e), mixing the mixture of MCT oil and molecularly separated cannabinoids with a terpene blend, wherein the terpene blend is selected to produce a target effect on the user, wherein the terpene blend of step f) consists of:
  a) Alpha-pinene at about 84.10 mg/g;
  b) Beta-caryophyllene at about 133.80 mg/g;
  c) Beta-pinene at about 52.90 mg/g;
  d) Humulene at about 54.50 mg/g;
  e) Myrcene at about 36.70 mg/g;
  f) Limonene at about 180.70 mg/g;
  g) Linalool at about 30.20 mg/g;
  h) Terpinolene at about 17.30 mg/g; and
  i) Other terpenoids at about 392.00 mg/g.

9. A method of producing an oral cannabis composition, the method consisting of the steps of:
 a) selecting a desired mixture of molecularly separated cannabinoids;
 b) after step a), mixing the molecularly separated cannabinoids with a heated MCT oil;
 c) after step b, cooling the mixture of the MCT oil and molecularly separated cannabinoids; and
 d) after step c, mixing the mixture of MCT oil and molecularly separated cannabinoids with a terpene blend;
 wherein the oral cannabis composition consists of:
  i) 500 mg of molecularly separated cannabinoids;
  ii) 14 ml of MCT oil; and
  iii) a terpene blend consisting of:
   1) Alpha-pinene at about 15.75 mg/g;
   2) Beta-caryophyllene at about 100.63 mg/g;
   3) Beta-pinene at about 15.75 mg/g;
   4) Humulene at about 26.25 mg/g;
   5) Myrcene at about 158.38 mg/g;
   6) Limonene at about 26.25 mg/g;
   7) Linalool at about 52.50 mg/g;
   8) Terpinolene at about 21.00 mg/g; and
   9) Other terpenoids at about 458.49 mg/g.

10. The method of claim 9, wherein the molecularly separated cannabinoids of step a) can either comprise naturally occurring cannabinoid amounts and/or ratios, or a specific formula and/or ratio of molecularly separated cannabinoids designed to achieve a desired effect for the end user.

11. A method of producing an oral cannabis composition, the method consisting of the steps of:
   a) selecting a desired mixture of molecularly separated cannabinoids;
   b) after step a), mixing the molecularly separated cannabinoids with a heated MCT oil;
   c) after step b, cooling the mixture of the MCT oil and molecularly separated cannabinoids; and
   d) after step c, mixing the mixture of MCT oil and molecularly separated cannabinoids with a terpene blend,
wherein the oral cannabis composition produced by the method consists of:
   a) 500 mg of molecularly separated cannabinoids;
   b) 14 ml of MCT oil; and
   c) a terpene blend consisting of:
      1) Alpha-pinene at about 269.37 mg/g;
      2) Beta-caryophyllene at about 109.66 mg/g;
      3) Beta-pinene at about 106.93 mg/g;
      4) Alpha-humulene at about 26.07 mg/g;
      5) Myrcene at about 352.62 mg/g;
      6) Alpha-bisabolol at about 18.21 mg/g;
      7) Borneol at about 1.8 t mg/g;
      8) Valencene at about 0.87 mg/g;
      9) Nerolidol at about 1.98 mg/g;
      10) Linalool at about 7.61 mg/g;
      11) Limonene at about 38.35 mg/g;
      12) Fenchol at about 4.04 mg/g;
      13) Alpha-phellandrene at about 16.76 mg/g;
      14) Caryophyllene Oxide at about 0.98 mg/g;
      15) Terpineol at about 3.68 mg/g;
      18) Citronellol at about 0.96 mg/g; and
      16) Phytol at about 17.08 mg/g.

12. A method of producing an oral cannabis composition, the method consisting of the steps of:
   a) selecting a desired mixture of molecularly separated cannabinoids;
   b) after step a), mixing the molecularly separated cannabinoids with a heated MCT oil;
   c) after step b, cooling the mixture of the MCT oil and molecularly separated cannabinoids; and
   d) after step c, mixing the mixture of MCT oil and molecularly separated cannabinoids with a terpene blend,
wherein the oral cannabis composition consists of:
   a) 500 mg of molecularly separated cannabinoids;
   b) 14 ml of MCT oil; and
   c) a terpene blend consisting of:
      1) Alpha-pinene at about 22.95 mg/g;
      2) Beta-caryophyllene at about 147.53 mg/g;
      3) Beta-pinene at about 2.97 mg/g;
      4) Alpha-humulene at about 228.05 mg/g;
      5) Myrcene at about 143.64 mg/g;
      6) Valencene at about 0.52 mg/g;
      7) Linalool at about 396.42 mg/g;
      8) Terpinolene at about 2.98 mg/g;
      9) Nerolidol at about 9.95 mg/g;
      10) Fenchol at about 0.97 mg/g;
      11) Alpha-phellandrene at about 7.86 mg/g; and
      12) Caryophyllene Oxide at about 12.35 mg/g.

13. A method of producing an oral cannabis composition, the method consisting of the steps of:
   a) selecting a desired mixture of molecularly separated cannabinoids;
   b) after step a), mixing the molecularly separated cannabinoids with a heated MCT oil;
   c) after step b, cooling the mixture of the MCT oil and molecularly separated cannabinoids; and
   d) after step c, mixing the mixture of MCT oil and molecularly separated cannabinoids with a terpene blend,
wherein the oral cannabis composition consists of:
   a) 500 mg of molecularly separated cannabinoids;
   b) 14 ml of MCT oil; and
   c) a terpene blend comprising consisting of:
      1) Alpha-pinene at about 246.02 mg/g;
      2) Beta-caryophyllene at about 4.66 mg/g;
      3) Beta-pinene at about 77.84 mg/g;
      4) Alpha-Humulene at about 6.05 mg/g;
      5) Myrcene at about 419.53 mg/g;
      6) Limonene at about 35.48 mg/g;
      7) Valencene at about 6.36 mg/g;
      8) Camphene at about 6.72 mg/g;
      9) Eucalyptol at about 22.08 mg/g;
      10) Alpha-phellandrene at about 23.59 mg/g;
      11) Caryophyllene Oxide at about 70.62 mg/g; and
      12) Phytol at about 0.25 mg/g.

14. A method of producing an oral cannabis composition, the method consisting of the steps of:
   a) selecting a desired mixture of molecularly separated cannabinoids;
   b) after step a), mixing the molecularly separated cannabinoids with a heated MCT oil;
   c) after step b, cooling the mixture of the MCT oil and molecularly separated cannabinoids; and
   d) after step c, mixing the mixture of MCT oil and molecularly separated cannabinoids with a terpene blend,
wherein the oral cannabis composition consists of:
   a) 500 mg of molecularly separated cannabinoids;
   b) 14 ml of MCT oil; and
   c) a terpene blend comprising consisting of:
      1) Alpha-pinene at about 84.10 mg/g;
      2) Beta-caryophyllene at about 133.80 mg/g;
      3) Beta-pinene at about 52.90 mg/g;
      4) Humulene at about 54.50 mg/g;
      5) Myrcene at about 36.70 mg/g;
      6) Limonene at about 180.70 mg/g;
      7) Linalool at about 30.20 mg/g;
      8) Terpinolene at about 17.30 mg/g; and
      9) Other terpenoids at about 392.00 mg/g.

* * * * *